(12) United States Patent
Chen (10) Patent No.: US 8,233,146 B2
(45) Date of Patent: Jul. 31, 2012

(54) CUVETTE FOR FLOW-TYPE PARTICLE ANALYZER

(75) Inventor: Yong Qin Chen, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 318 days.

(21) Appl. No.: 12/652,676

(22) Filed: Jan. 5, 2010

(65) Prior Publication Data

US 2010/0177305 A1    Jul. 15, 2010

Related U.S. Application Data

(60) Provisional application No. 61/205,051, filed on Jan. 13, 2009.

(51) Int. Cl.
*G01N 1/10* (2006.01)
(52) U.S. Cl. ........................................ 356/246
(58) Field of Classification Search .................. None
See application file for complete search history.

(56) References Cited

U.S. PATENT DOCUMENTS

| | | |
|---|---|---|
| 3,649,829 A | 3/1972 | Randolph |
| 4,088,407 A | 5/1978 | Schoeffel et al. |
| 4,643,570 A | 2/1987 | Machler et al. |
| 4,823,168 A | 4/1989 | Kamahori et al. |
| 4,989,974 A | 2/1991 | Anton et al. |
| 5,414,508 A | 5/1995 | Takahashi et al. |
| 5,484,571 A | 1/1996 | Pentoney, Jr. et al. |
| 5,815,258 A | 9/1998 | Nakanishi |
| 5,819,948 A | 10/1998 | van den Engh |
| 5,844,686 A | 12/1998 | Treptow et al. |
| 6,070,973 A | 6/2000 | Sachs et al. |
| 6,162,341 A | 12/2000 | Nordman et al. |
| 6,365,106 B1 | 4/2002 | Nagai |
| 6,396,584 B1 | 5/2002 | Taguchi et al. |
| 6,473,171 B1 | 10/2002 | Buttry et al. |
| 6,597,438 B1 | 7/2003 | Cabuz et al. |
| 6,873,411 B2 * | 3/2005 | Sebok et al. .................. 356/335 |
| 7,064,823 B2 | 6/2006 | Roche et al. |
| 7,201,875 B2 | 4/2007 | Norton et al. |
| 7,277,167 B2 | 10/2007 | Schembri et al. |
| 7,320,775 B2 | 1/2008 | Kochy et al. |
| 7,332,128 B2 * | 2/2008 | Fernando et al. ............. 422/501 |
| 2005/0180885 A1 | 8/2005 | Tateishi et al. |

FOREIGN PATENT DOCUMENTS

| | | |
|---|---|---|
| WO | WO0127590 | 4/2001 |
| WO | WO03002985 | 1/2003 |

OTHER PUBLICATIONS

S. M. Jayasinghe et al., "Sterile and Disposable Fluidic Subsystem Suitable for Clinical High Speed Fluorescence-Activated Cell Sorting," Cytometry Part B (Clinical Cytometry), vol. 70B: 344-354 (2006).
D. Peters et al., "The LLNL High-Speed Sorter: Design Features, Operational Characteristics, and Biological Utility," Cytometry, vol. 6: 290-301 (1985).

(Continued)

*Primary Examiner* — Tu Nguyen
(74) *Attorney, Agent, or Firm* — Douglas A. Petry (57) ABSTRACT

The present invention provides an optical cuvette for use in a flow-type particle analyzer, wherein the cuvette includes a removable flow tube containing a flow channel oriented coaxially.

11 Claims, 6 Drawing Sheets

OTHER PUBLICATIONS

H. M. Shapiro et al., "Multistation Multiparameter Flow Cytometry: Some Influences of Instrumental Factors on System Performance," Cytometry, vol. 4: 11-19 (1983).

J. T. Soini et al., "A New Design of the Flow Cuvette and Optical Set-Up for the Scanning Flow Cytometer," Cytometry, vol. 31: 78-84 (1998).

* cited by examiner

CUVETTE FOR FLOW-TYPE PARTICLE ANALYZER

BACKGROUND OF THE INVENTION

1. Field of the Invention

The present invention relates to the field of optical analysis of fluid streams and, in particular, to flow-type particle analyzers, such as flow cytometers, and particle sorting systems.

2. Description of Related Art

Flow-type particle analyzers, such as flow cytometers, are well known analytical tools that enable the characterization of particles in a fluid stream on the basis of optical parameters such as light scatter and fluorescence. In a flow cytometer, particles such as molecules, analyte-bound beads, or individual cells in a fluid suspension are passed by one or more detectors in which the particles are exposed to an excitation light, typically from one or more lasers, and the light scattering and fluorescence properties of the particles are measured. Each particle, or subcomponents thereof, may be labeled with a multiplicity of spectrally distinct fluorescent dyes. Typically, detection or characterization is carried out using a multiplicity of photodetectors, one for each distinct dye to be detected.

Flow-type particle sorting systems, such as sorting flow cytometers, are used to sort particles in a fluid sample based on the characterization of the particles. In a flow-type particle sorting system, the fluid stream is jetted from a nozzle and a droplet generator vibrates fluid stream to break the stream into uniform discrete drops after optical analysis. When a particle of the type to be sorted is detected, a sorting mechanism is triggered to separate the drop containing the particle from the stream of drops. A number of methods of sorting particles are known in the art, including the use of moving droplet capture tubes (as described in U.S. Pat. No. 5,030, 002) and electrostatic sorting. In electrostatic sorting, drop charging means are connected to the stream to charge drops containing a particle of the type to be sorted with an electrical charge as it breaks off from the jet stream. The stream of drops is passed through a transverse electrostatic field established by a pair of oppositely charged deflection plates. Uncharged drops are not deflected passing through the electrostatic field and are collected by a central receptacle. Charged drops containing a particle of the type to be sorted are deflected in a direction and amount related to the polarity and magnitude of the drop charge and are collected in a separate collection receptacle.

Optical analysis of particles using a sorting flow cytometer typically is carried out after the stream has been jetted from the nozzle. Alternatively, the analysis is carried out while the fluid stream is passing through a channel in an optical cuvette, as is typically used in an analyzing flow cytometer. Sorting flow cytometers that use a cuvette for optical analysis are described in, for example, U.S. Pat. Nos. 4,660,971 and 7,201,875; the entire contents of both patents incorporated herein by reference.

Flow cytometers and sorting flow cytometers are described in Shapiro, 2003, Practical Flow Cytometry (John Wiley and Sons, Inc. Hoboken, N.J.); and "Flow Sorters for Biological Cells" by Tore Lindmo, Donald C. Peters, and Richard G. Sweet, Flow Cytometry and Sorting, 2d ed. (New York: Wiley-Liss, Inc., 1990), pages 145-169, both incorporated herein by reference. Flow cytometers and sorting flow cytometers are commercially available from, for example, BD Biosciences (San Jose, Calif.).

In a number of applications in flow cytometry, such as sorting of cells for therapeutic use, it is desirable to sterilize or replace the fluidic path after each use. Replacement of the components of the fluidic path typically requires realignment of the excitation and detection optics, which is both time-consuming and difficult.

BRIEF SUMMARY OF THE INVENTION

The present invention provides a cuvette for use in a flow-type particle analyzer that analyzes particles as they pass in a fluid stream through a flow channel within the cuvette, wherein the cuvette includes a removable flow tube that contains the flow channel. The cuvette comprises a cuvette block containing a sleeve channel, which is a through-hole extending through the cuvette block, with openings at opposite sides of the cuvette block. The flow tube containing the flow channel, oriented coaxially, is removably inserted into the sleeve channel. The removable flow tube containing the flow channel facilitates sterilization of the flow path by allowing replacement of the flow cell elements that come in contact with the sample without having to realign the optics of the system.

The present invention further provides a flow cell comprising the cuvette of the present invention. The flow cell includes a flow cell chamber, a sample input port, optionally at least one sheath input port, and a cuvette comprising a removable flow tube containing a flow channel oriented coaxially. The flow tube can be formed as a tubular extension of the flow cell chamber or as a separate flow tube that is joined to the flow chamber, such that the flow channel communicates with the interior of the flow chamber. The sheath flow and sample stream flow out of the flow cell chamber through the flow channel in the flow tube.

Optical analysis of the particles in the sample stream is carried out in a detection region in the flow channel that runs through the flow tube, which is held in the sleeve channel of the cuvette. At least a portion of the cuvette and flow tube are optically transparent such that excitation light from outside the cuvette can be transmitted to the detection region and light emitted from the detection region can be measured by photodetectors positioned outside the cuvette.

In some embodiments, the cuvette is be joined directly to the flow cell chamber, and the flow tube can be replaced separately. In other embodiments, the cuvette and the flow cell are not directly coupled together, and either the flow tube or the flow cell body containing an integral flow tube can be replaced. Where the flow tube is separately replaceable, the flow tube and flow cell body are adapted to form a seal between the flow cell chamber and the flow channel when the flow tube is inserted into position.

An advantage of the present invention is that the cuvette can be mounted in the instrument in a fixed position and coupled directly to the excitation and/or detection optics, and the flow tube can be replaced conveniently without disturbing the alignment of the optics with the cuvette.

The cuvette of the present invention, having a replaceable flow tube, can be adapted for use in a sorting flow cytometer. A sorting flow cytometer includes a droplet generator, such as a piezo-electric oscillator, that applies a vibratory force, directly or indirectly, to the fluid sample stream and causes the fluid sample stream to break into droplets after leaving the flow channel. In some embodiments, the droplet generator is adapted to indirectly impart oscillating pressure waves to the sample stream by vibrating an element on the flow cell or flow tube. In other embodiments, the droplet generator is adapted to impart a vibratory force directly to the sample stream, thereby minimizing vibrations of the flow cell or cuvette.

In one embodiment, the cuvette and the flow cell chamber are not directly coupled together, and the oscillator is adapted to apply a vibratory force to the flow cell chamber or to the flow tube. Preferably, the oscillations are along the flow channel axis. Because the flow tube is movable within the sleeve channel of the cuvette, vibrations of the flow cell are largely isolated from the optical cuvette and do not interfere with the stability of the excitation and/or detection optics. Additionally, vibrations applied to the flow tube can be isolated from the flow cell chamber, or vice versa, by using a connector between the flow tube and the flow cell chamber that allows independent movement of the flow tube.

In another embodiment, the droplet generator is adapted to apply oscillating forces that are radial to the axis of the flow tube. The oscillator can be a piezoelectric crystal in the shape of a ring surrounding the outside of the flow tube, operating in a radial mode. The piezoelectric ring operating in a radial mode about the flow tube alternately compresses and releases the outer surface of the nozzle tubing, sufficient to set up regular oscillations on the surface of the sheathed sample stream. A droplet generator using a piezoelectric oscillator that applies radial, compressive oscillations is described in U.S. Pat. No. 6,070,973, incorporated herein by reference. The use in a sorting flow cytometry of a piezoelectric ring operating in a radial mode to provide a vibratory force to the fluid stream is described in U.S. Patent Application Publication No. US 2007/0269348, incorporated herein by reference.

In preferred embodiments, the cuvette will have flat external surfaces to facilitate use with the excitation and detection optics. Optical elements, such as a lens or minor, can be joined to the cuvette or molded as part of the cuvette block (see, for example, WO 01/27590, incorporated herein by reference). The cuvette may also contain additional features that facilitate positioning the cuvette.

In some embodiments, the flow channel within the flow tube has a rectangular cross-sectional shape. In order to fix the orientation of the flow channel relative to the excitation and detection optics, the flow tube and/or the cuvette will include a means to prevent rotation of the flow tube around the axis of the flow channel. In one embodiment, the flow tube will have a flat key or slot that facilitates positioning the flow tube in a precise angular position. Alternatively, the flow tube and sleeve channel can have cross-sectional shapes that prevent rotation of the flow tube around the flow channel axis. In some applications, it may be desirable to include a rotational position adjusting mechanism to insure the desired rotational position of the flow tube with respect to the cuvette and optics.

In the present invention, significant advantage is derived from a configuration in which the position of the cuvette is fixed to the instrument. Because the optical cuvette need not be moved, other optical elements that must be focused or positioned relative to the cuvette also can be fixed in position. The cuvette can be joined to other optical elements, such as a focusing lens adapted to focus the excitation light onto the detection region, or a lens of mirror adapted to collect light emitted from the detection region, e.g., using a gel or optical fluid to fill any gaps between the optical elements and the surface of the cuvette. The use or a removable flow tube enable replacement of the flow tube/flow channel without effecting the alignment or joined mounting of the optical elements. A precision fit between the sleeve channel and the flow tube maintains that position of the flow channel relative to the optics. Furthermore, when used in a sorting flow cytometer, the oscillations applied to the flow cell or the flow tube can be isolated from the cuvette.

DETAILED DESCRIPTION OF THE INVENTION

The following definitions are provided for clarity. Unless otherwise indicated, all terms are used as is common in the art. All reference cited herein, both supra and infra, are incorporated herein by reference.

A "flow-type particle analyzer" is used herein to refers to any instrument that analyzes particles suspended in a flowing fluid stream by passing the particles past one or more optical detectors, and includes, for example, analyzing or sorting flow cytometers, hematology analyzers, and cell counters.

An "index-matching material" refers to a substance, usually a liquid, cement (adhesive), or gel, that has an index of refraction that equals or closely approximates that of an optical element. Index-matching material typically is used to reduce optical and chromic aberrations, and to reduce Fresnel reflections, caused by a refractive discontinuity at the surface of an optical element. For example, in the present invention, an index-matching material preferably can be used to fill any gap between the inner surface of the sleeve channel and the outer surface of the flow tube. An index-matching material can also be used to optically couple the components of a cuvette block constructed from multiple components such that the final cuvette acts as if it were made from a single component.

Index-matching materials are well-known in the art and are commercially available from a number of vendors (for example, Cargille Laboratories, Cedar Grove, N.J.). Using mixtures of the available index-matching materials, an index-matching material have an index of refraction the closely matches the index of refraction of the material (e.g., glass) used in the manufacture of the cuvette can be produced routinely.

At least a portion, preferably all, of the cuvette and flow tube are optically transparent to enable optical detection of particles within the flow stream. For example, in a flow cytometer, optical detection typically is carried out by exciting fluorescently labeled particles using an excitation light from outside the cuvette, and the fluorescence emissions from the particles are detected using photodetectors positioned outside the cuvette. The optically transparent portion of a cuvette can be made from any suitable material, including fused silica, quartz, optical glass, or an optical grade plastic.

An advantage of the cuvette and removable flow tube of the present invention is that they can be constructed using precision components commercially available for use in the telecommunications and photonic industries, in particular, fiber optic ferrules and collimator sleeves used in fiber optic connectors. Optical fibers are used in the telecommunication industry for high-speed data transmissions. Typically, optical fibers of silica glass or other suitable material are clad with an appropriate material to create a waveguide along which light can travel in a controlled manner. Fiber optic connectors are used to couple optical fibers with another optical fibers or with optical devices (e.g., electro-optic and opto-electric devices). Fiber optic connectors must be high-precision parts to ensure the fiber is optimally aligned in order to minimize scatter of the light signal and consequent damping or loss of signal. Components used in fiber optic connectors that may be usable in the present invention include ferrules and collimator sleeves. An important feature of fiber optic components is their dimensional accuracy to support a minimal dB loss. Precision glass fiber optic connector components suitable for use in the present invention are commercially available, either as off-the-shelf products, or as custom products, from a number of vendors, such as BD Diagnostics—Accu-Glass (St. Louis, Mo.) and VitroCom (Mountain Lakes, N.J.).

A fiber optic ferrule is a tube with a central passage which receives the fiber for connection. The ferrule permits positioning of the optical fiber held by the connector to receive and transmit signals another optical fiber or optical light source. Usually, one or more optical fibers pass through the ferrule, and the dimensions of the central passage will depend on the number and size of the optical fibers. Ferrules made from precision-drawn borosilicate tubing, suitable for use in the present invention are commercially available from, for example, BD Diagnostics—Accu-Glass. The precision of these commercially available parts is high. For example, BD Diagnostics—Accu-Glass manufactures a ferrule that has an inside diameter of 127 microns with a tolerance of +/−1 micron. The tubing can be precision cut to length using a process which employs diamond blades. In addition, fiber optic ferrules that have inner funnel formed in one end of the central passage to facilitate inserting the fiber into the ferrule are commercially available (also from, for example, BD Diagnostics—Accu-glass). Custom inside diameter, outside diameter, length and funnel options are commercially available.

Collimator sleeves are high-precision tubes that align other internal optical components. For example, an optical fiber is inserted into ferrule, and the ferrule is inserted into the collimator sleeve. Typically, collimator sleeves are 10 mm in length, although collimator sleeves are commercially available in a wide range of lengths. The dimensional accuracy of commercially available collimator sleeves and ferrules provides precise slip-fit components.

Collimator sleeves and ferrules are useable in the present invention as sleeve tubes and flow tubes, respectively, as described below with respect to the figures. The gap between the sleeve tube and flow tube preferably is filled with an index-matching fluid to reduce optical aberrations and to lubricate the flow tube such that it is easier to insert into the sleeve tube.

Description Based on the Figures

Figure 1:
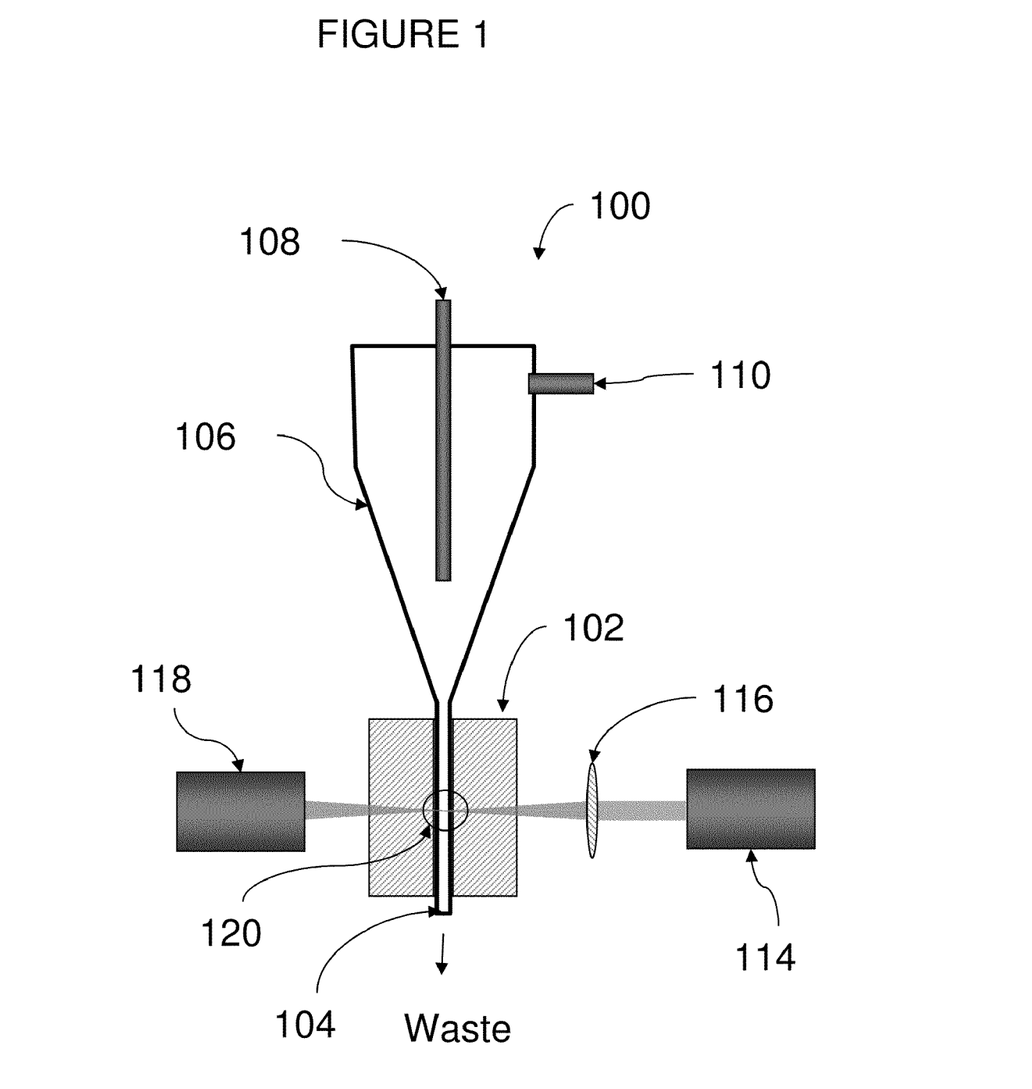
FIG. 1 shows a cross-sectional view of elements of a flow cytometer employing an apparatus according to an embodiment of the present invention.

FIG. 1

FIG. 1 depict elements of a flow cytometer incorporating a flow cell of the present invention. Flow cell 100 includes flow cell chamber 106, sample inlet port 108, and a sheath inlet port 110. The sample inlet port 108 and sheath inlet port 110 are adapted to provide particle-containing fluid sample and particle-free sheath fluid, respectively, into the flow cell chamber 106. Flow cell chamber 106 converges to an opening that is joined to flow tube 104, which contains a flow channel coaxially oriented through the flow tube, such that the interior of the flow chamber smoothly communicates with the flow channel. As depicted, flow tube 104 is formed as a tubular extension of the flow cell chamber 106, but can be formed as a separate tube that is then joined to the flow cell chamber.

Cuvette 102 contains a through-hole ("sleeve channel") into which flow tube 104 is inserted. The cross-sectional shape of the sleeve channel matches the cross-sectional shape of the flow tube, but is sufficiently larger in size to permit insertion and removal of the flow tube while minimizing the gap between the outer surface of the flow tube and the inner surface of the sleeve channel. An index-matched fluid (not shown) is used to fill this gap to minimize light loss at the material junctions.

In use, sample fluid containing the particles to be analyzed is introduced into the flow cell 100 through sample inlet port 108, and particle-free sheath fluid is introduced into the flow cell through sheath inlet port 110. Fluids exit through flow tube 104 and are directed to a waste receptacle (not shown). The flow cell is designed such that the sheath fluid forms and annular flow coaxial with the sample fluid, thereby creating a hydrodynamically focused flow of particle-containing sample fluid in the center of the fluid stream, surrounded by particle-free sheath fluid. The combined fluid stream consisting of sheath fluid and sample fluid is referred to herein as the "sample stream", "flow stream" or "particle stream". Although hydrodynamic focusing using a sheath fluid is commonly used in the field of flow cytometry, it is not essential, and is omitted in some flow cytometers. In such "sheathless" flow cytometers, the sample stream consists solely of a stream of the particle-containing sample fluid.

Optical analysis of the particles within the sample stream is carried out by exposing the sample stream in detection region 120 to excitation light and detecting light emanating from the detection region 120. Excitation light source 114 emits a beam of light that is focused by lens 116 onto the sample stream at detection region 120 (also known as the observation region or interrogation point). Photodetector 118 is positioned to detect light emitted from the detection region 120. Cuvette 102 is constructed, at least in part, from an optically clear material to enable optical excitation and detection.

Although a single detector is shown, more typically, multiple detectors are present, and include detector positioned to detect excitation light that is scattered by particles at a low angle relative to the excitation beam, referred to as forward scatter light, excitation light that is scattered by particles at nearly right angles to the excitation beam, referred to as side scatter light, and fluorescent light emitted from particles in the sample stream. Suitable photodetectors for use in a flow-type particle analyzer include, for example, photomultiplier tubes (PMTs), avalanche photo diodes, photodiodes, or any other suitable light-detecting device.

Figure 2A:
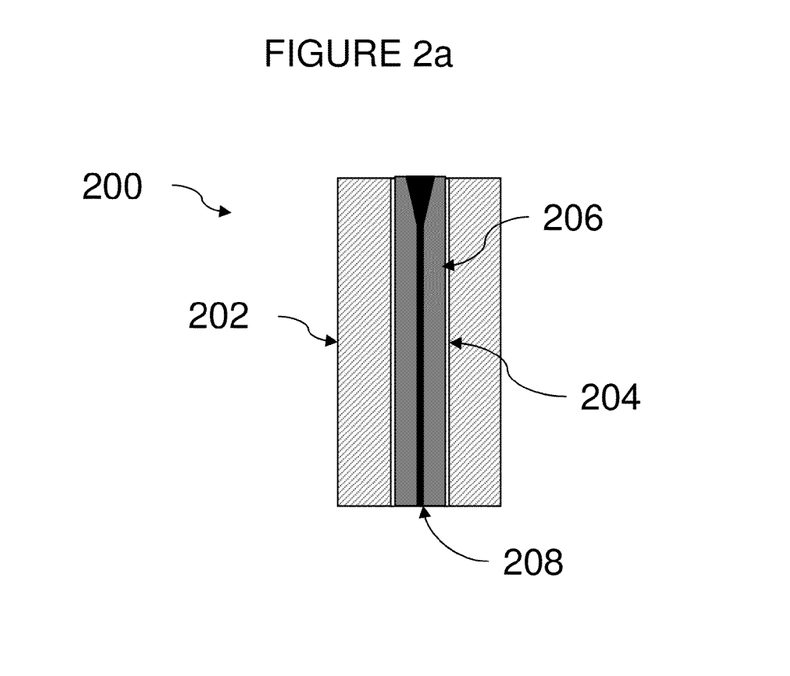
FIG. 2a shows a cross-sectional view of an embodiment of the cuvette of the present invention.
Figure 2B:
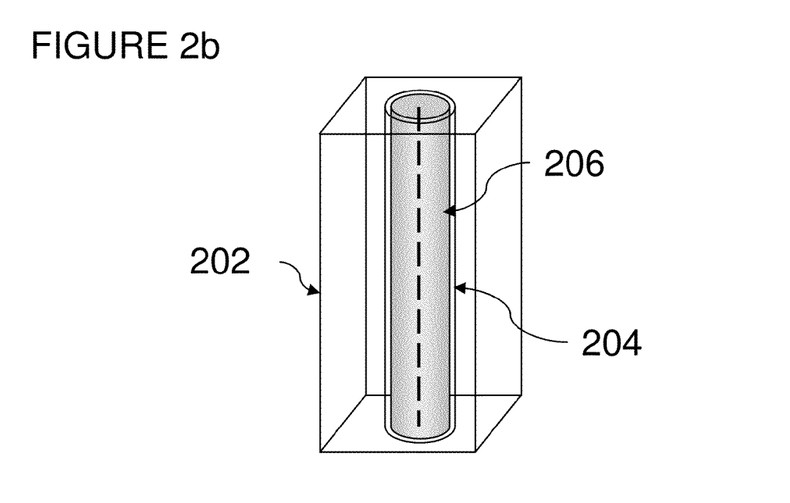
FIG. 2b shows an angled view of the cuvette.

FIG. 2

FIGS. 2a and 2b show an embodiment of the cuvette of the present invention. Cuvette 200 comprises a cuvette block 202 made of an optically transmissive material, such as fused silica, glass, clear plastic or any other suitable material, having a sleeve channel 204 through it. Flow tube 206, also made of a optically transmissive material, and containing flow channel 208 oriented coaxially, is positioned in the sleeve channel. Preferably, the flow tube and the cuvette block are made of materials having the same refractive index.

The cuvette shown in FIGS. 2a and 2b is orientated such that the sample fluid flows from top to bottom. The flow channel 208 is shown in FIG. 2a as having an optional widening of the channel at the top, inlet end that facilitates connecting the flow channel to the flow cell chamber (element 106 depicted in FIG. 1).

As shown, the flow tube 206 is cylindrical in shape, and the sleeve channel 204 is cylindrical with a diameter sufficiently larger than the diameter of the flow tube to enable insertion and removal of the flow tube. Preferably, the gap between the flow tube and the sleeve channel is filled with an index-matched fluid, which eliminates optical distortion at the interfaces between the cuvette block and the flow tube and the gap between the two. The index-matched fluid further acts as a lubricant, facilitating the insertion and removal of the flow tube.

Although the flow tube 206 is shown as cylindrical in shape, i.e., having a circular cross-sectional shape, the cross-sectional shape of the flow tube is not a critical aspect of the invention. In some embodiments, it will be desirable to use a flow tube having a cross-sectional shape that prevents rotation of the flow tube within the sheath channel. For example, in embodiments in which the flow channel is rectangular in cross-section, a cross-sectional shape for the flow tube that prevents rotation will enable consistent orientation of the flow channel relative to the excitation and detection optics. Alternatively, a feature, such as a slot or flattened portion, can be machined into the flow tube to enable consistent orientation of the flow tube.

Figure 3:
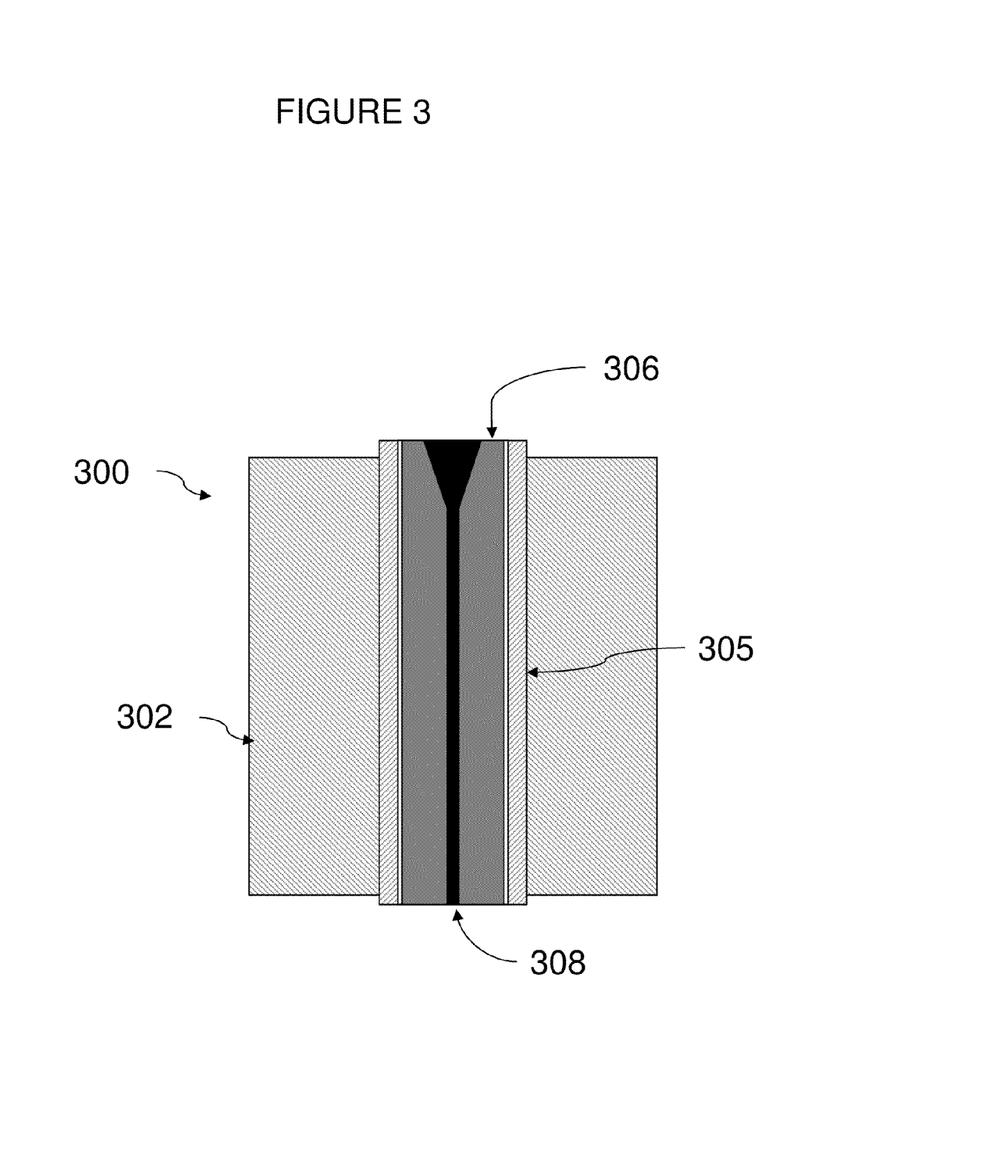
FIG. 3 shows a cross-sectional view of an alternative embodiment of the cuvette of the present invention.

FIG. 3

FIG. 3 shows a side cross-sectional view of an embodiment of the cuvette of the invention in which the sleeve channel is formed by a separate sleeve tube 305 that passes through the cuvette block 302. The cuvette block may be molded around the sleeve tube, or manufactured with a hole extending through the cuvette block such that the sleeve tube can be inserted into the cuvette block to form essentially a single block. The use of a separate sleeve tube can simplify the manufacture of the cuvette block.

Figure 4A:
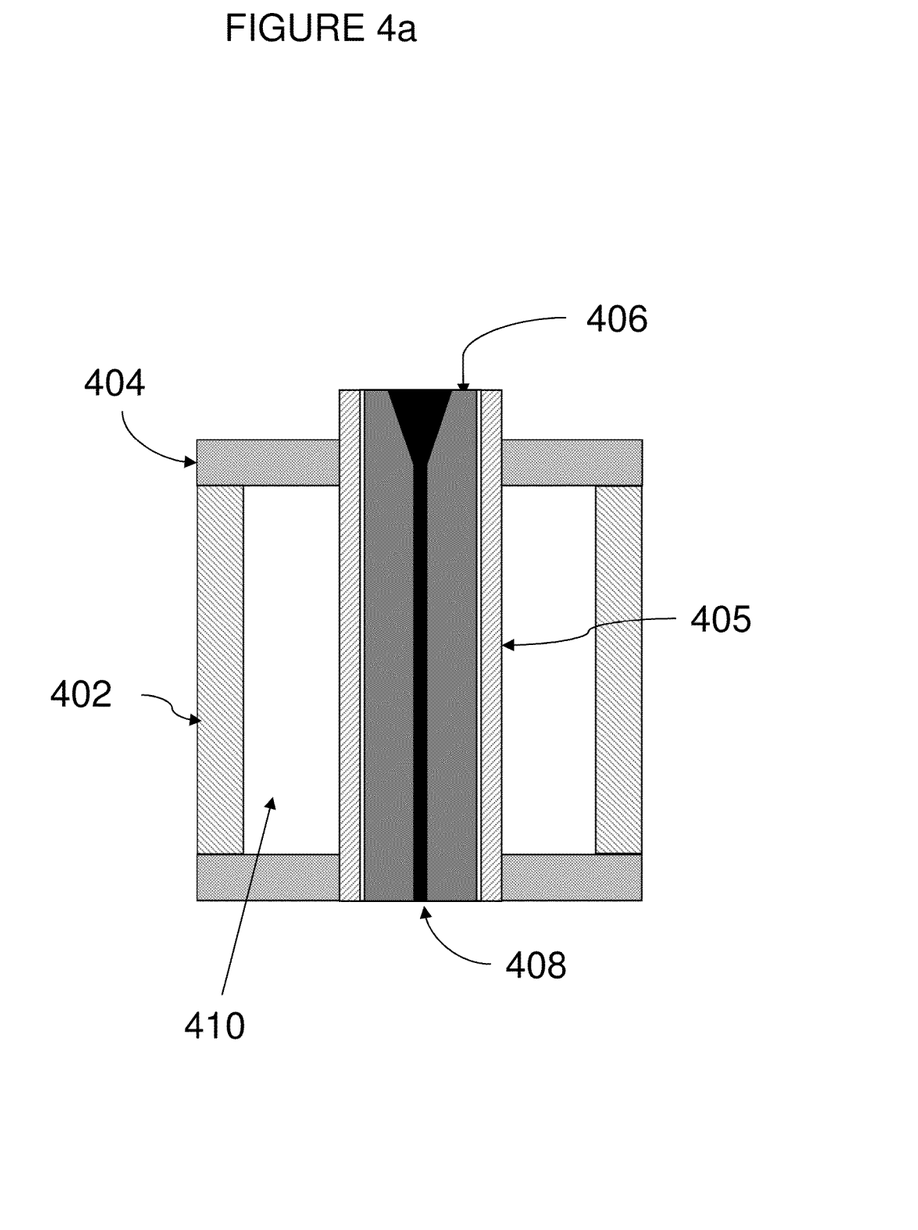
FIG. 4a shows a cross-sectional view of an alternative embodiment of the cuvette of the present invention.
Figure 4B:
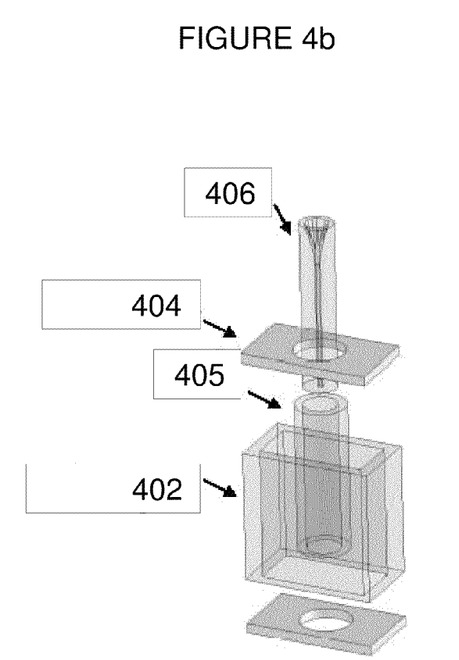
FIGS. 4b and 4c show an exploded view and an assembled view of the cuvette, respectively.
Figure 4C:
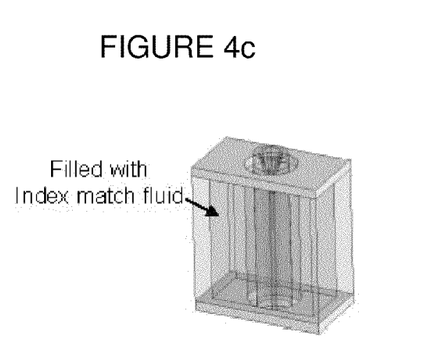

FIG. 4

FIG. 4a shows a frontal view of another embodiment of a cuvette of the present invention in which the sleeve channel is formed by a separate tube 405 that passes through the cuvette block, and the cuvette block is formed from multiple components. FIG. 4b shows an exploded view of the components of the cuvette. FIG. 4c shows an assembled view of the components of the cuvette.

The cuvette block is constructed of a length of an outer tube 402 having a rectangular cross-sectional shape. The top and bottom of outer tube 402 are capped with plates 404 bonded to the outer tube to form a box-shaped interior cavity 410. Sleeve tube 405 is positioned to extend through the interior cavity 410, extending through holes in the top and bottom plates. The holes in the plates have a diameter matching the outside diameter of the sleeve tube and function both to position the sleeve tube in the interior cavity and to seal the interior cavity. Flow tube 406 having a flow channel 408 passing coaxially through the tube is inserted into the sleeve tube. Flow channel 408 includes an optional widening of the channel at the top, inlet end that facilitates connecting the flow channel to a flow cell chamber.

Preferably, the outer tube 402, the sleeve tube 405, and the flow tube 406 are constructed from the same type of material so that the index of refraction of these three elements are the same. Cavity 410 is filled with an index-matching fluid that matches the index of refraction of these three elements, resulting in a cuvette block that behaves optically as if constructed of single, homogeneous material.

Figure 5:
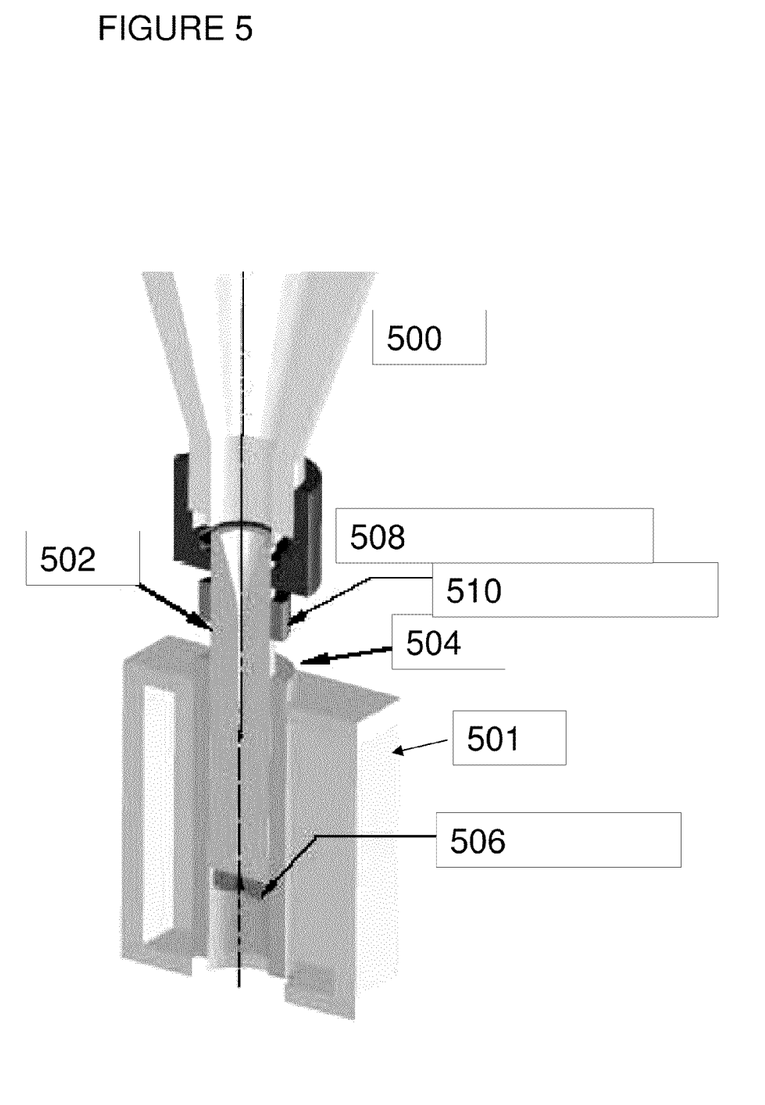
FIG. 5 shows a cross-sectional view of an embodiment of a flow cell and cuvette of the present invention adapted for use in a sorting flow cytometer.

FIG. 5

FIG. 5 shows a angled, cross-sectional view of a flow cell and cuvette adapted for use in a sorting flow cytometer. Cuvette block 501 is constructed from multiple components in the same manner as described above for the cuvette block shown in FIG. 4. Flow tube 502 is connected to flow cell chamber 500 using a quick connector 508 having an O-ring seal. The inside diameter of the flow cell chamber at its terminus matches the diameter of the inlet of the flow channel (depicted as including a funnel shaped opening) so as to form a smooth transition. An orifice 506, preferably constructed from a sapphire or ruby, is glued to the end of the flow tube to form a nozzle.

A droplet generator 510 consisting of a piezoelectric element is attached to the outside of the flow tube. Preferably, the droplet generator is adapted to vibrate the flow tube along the axis of the flow channel. Because the flow tube is free to move within the sleeve channel, vibrations of the flow tube along the axis of the flow channel will not be transmitted to the cuvette. Connector 508 is adapted to allows vibration of the flow tube without breaking the seal formed by the O-ring.

EXAMPLE 1

Cuvette for use in a Sorting Flow Cytometer

A flow cell and cuvette essentially as shown in FIG. 5 and described, above, was constructed using standard optical components commercially available for use in the telecommunication and photonics industries.

A fiber optic ferrule with a rectangular core 127 μm×254 μm was used the flow tube. A fiber optic collimator sleeve designed for use with the ferrule was used as the sleeve tube. The ferrule fitted into the collimator sleeve such that the gap between the ferrule and the collimator sleeve was less than 5 μm. The gap was filled with index-matching fluid using capillary effect. The index-matching fluid also functioned as a lubricant to facilitate the insertion and removal of the ferrule into the sleeve.

The cuvette block was constructed from borosilicate glass tubing having a rectangular cross-section. Plastic covers on the top and bottom, each having a central hole sized to fit the sleeve tube, were glued to each end of the rectangular glass tube. The sleeve tube was glued to the plastic covers such that the sleeve tube was held in the interior of the cuvette block with the flow channel running through the cuvette block. The interior of the cuvette block was filled with index-matching fluid.

A piezoelectric oscillator (droplet generator) was attached to the outside of the flow cell chamber above the cuvette, adapted to vibrate the flow cell chamber and the connected flow tube.

The flow cell and cuvette was connected to a sample fluid source and a sheath fluid source, and the resulting flow cell and cuvette assembly was used to form a stream of droplets under the control of the droplet generator.

I claim:

1. An optical cuvette for use in a flow-type particle analyzer, comprising:
    a cuvette block containing a sleeve channel extending through said cuvette block;
    a flow tube adapted to be removably inserted into said sleeve channel of said cuvette block to form a slip-fit, wherein said flow tube contains a flow channel passing coaxially through said flow tube,
    wherein at least a portion of said cuvette block and said flow tube are optically transmissive such that an excitation light can be transmitted through said cuvette block and flow tube to a detection region within said flow channel.

2. A flow-type particle analyzer, comprising:
an optical cuvette of claim 1;
excitation optics configured to transmit excitation light to a detection region located within said flow channel;
detection optics configured to detect light emitted from said detection region;
wherein said optical cuvette is fixed in position within said particle analyzer.

3. A flow-type particle analyzer of claim 2, wherein at least one of said excitation optics and said detection optics is coupled to said optical cuvette.

4. An optical cuvette for use in a flow-type particle analyzer, comprising:
a cuvette block;
a sleeve tube passing through the interior of the cuvette block, containing a sleeve channel;
a flow tube adapted to be removably inserted into said sleeve channel of said cuvette block to form a slip-fit, wherein said flow tube contains a flow channel passing coaxially through said flow tube,
wherein at least a portion of said cuvette block, said sleeve tube, and said flow tube are optically transmissive such that an excitation light can be transmitted through said cuvette block and flow tube to a detection region within said flow channel.

5. An optical cuvette of claim 4, wherein said cuvette block comprises
a tube-shaped body consisting of an optically transmissive solid, having a rectangular cross-sectional shape and having a first and a second end;
a top plate at the first end of said tube-shaped body; and
a bottom plate at the second end of said tube-shaped body;
wherein said sleeve tube passes through said top plate and said bottom plate such that the tube-shaped body, the top plate, the bottom plate, and the sleeve tube form a sealed interior cavity, and
an optically transmissive fluid contained in the sealed interior cavity, wherein the tube-shaped body, the sleeve tube, and the optically transmissive fluid have indices of refraction that are approximately the same.

6. A flow-type particle analyzer comprising, comprising:
an optical cuvette of claim 4;
excitation optics configured to transmit excitation light to a detection region located within said flow channel;
detection optics configured to detect light emitted from said detection region;
wherein said optical cuvette is fixed in position within said particle analyzer.

7. A flow-type particle analyzer of claim 6, wherein at least one of said excitation optics and said detection optics is coupled to said optical cuvette.

8. A flow cell for use in a flow-type particle analyzer, comprising
(a) a flow cell chamber, comprising
a sample inlet port,
a sheath inlet port, and
a fluid exit opening; and
(b) an optical cuvette, comprising
a cuvette block containing a sleeve channel extending through said cuvette block;
and
a flow tube adapted to be removably inserted into said sleeve channel of said cuvette block to form a slip-fit, wherein said flow tube contains a flow channel passing coaxially through said flow tube,
wherein at least a portion of said cuvette block and said flow tube are optically transmissive such that an excitation light can be transmitted through said cuvette block and flow tube to a detection region within said flow channel;
wherein said fluid exit opening of said flow cell chamber is in fluid communication with said flow channel contained in said flow tube.

9. A flow cell of claim 8, wherein said optically transmissive portion of said cuvette block has a rectangular cross-section.

10. A flow cell of claim 8, additionally comprising a droplet generator adapted to vibrate at least one component of said flow cell.

11. A flow cell of claim 8, additionally comprising a droplet generator adapted to vibrate fluid contained in said flow cell chamber.

* * * * *